US010166279B2

(12) United States Patent
Puntervoll et al.

(10) Patent No.: US 10,166,279 B2
(45) Date of Patent: Jan. 1, 2019

(54) VACCINE

(71) Applicants: Bergen Teknologioverføring AS, Bergen (NO); The Administrators of the Tulane Educational Fund, New Orleans, LA (US)

(72) Inventors: Pål Puntervoll, Bergen (NO); Halvor Sommerfelt, Bergen (NO); John Clements, New Orleans, LA (US); James P. Nataro, Bergen (NO); Weiping Zhang, Manhattan, KS (US); Arne M. Taxt, Bergen (NO)

(73) Assignees: Bergen Teknologioverføring, Bergen (NO); The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/769,342

(22) PCT Filed: Feb. 20, 2014

(86) PCT No.: PCT/IB2014/000267

§ 371 (c)(1),
(2) Date: Aug. 20, 2015

(87) PCT Pub. No.: WO2014/128555

PCT Pub. Date: Aug. 28, 2014

(65) Prior Publication Data

US 2016/0220654 A1 Aug. 4, 2016

Related U.S. Application Data

(60) Provisional application No. 61/766,958, filed on Feb. 20, 2013, provisional application No. 61/767,161, filed on Feb. 20, 2013, provisional application No. 61/850,636, filed on Feb. 20, 2013, provisional application No. 61/886,242, filed on Oct. 3, 2013.

(51) Int. Cl.

| | |
|---|---|
| ***A61K 39/108*** | (2006.01) |
| ***C07K 14/245*** | (2006.01) |
| ***C07K 16/12*** | (2006.01) |
| *A61K 39/00* | (2006.01) |

(52) U.S. Cl.

CPC ........ *A61K 39/0258* (2013.01); *C07K 14/245* (2013.01); *C07K 16/1232* (2013.01); *A61K 2039/52* (2013.01)

(58) Field of Classification Search

None

See application file for complete search history.

(56) References Cited

U.S. PATENT DOCUMENTS

| | | | |
|---|---|---|---|
| 4,912,094 | A | 3/1990 | Myers et al. |
| 4,987,237 | A | 1/1991 | Myers et al. |

FOREIGN PATENT DOCUMENTS

| | | | |
|---|---|---|---|
| WO | 1999/009416 | A2 | 2/1999 |
| WO | 2005/087797 | A1 | 9/2005 |
| WO | 2010/048322 | A1 | 4/2010 |

OTHER PUBLICATIONS

Liu M, et al. "Modified heat-stable toxins (hSTa) of enterotoxigenic *Escherichia coli* lose toxicity but display antigenicity after being genetically fused to heat-labile toxoid LT(R192G)." Toxins, 3(9):1146-62 (Sep. 15, 2011).

Okamoto K, et al. "Reduction of enterotoxic activity of *Escherichia coli* heat-stable enterotoxin by substitution for an asparagine residue." Infection and Immunity, 56(8):2144-8 (Aug. 1988).

Taxt A, et al. "Heat-stable enterotoxin of enterotoxigenic *Escherichia coli* as a vaccine target." Infection and Immunity, 78(5):1824-31 (May 2010; published online Mar. 15, 2010).

Yamasaki S, et al. "Structure-Activity Relationship of *Escherichia coli* Heat-Stable Enterotoxin: Role of Ala Residue at Position 14 in Toxin-Receptor Interaction." Bulletin of the Chemical Society of Japan, 63(7):2063-2070 (Jul. 1990).

Zhang W, et al. "Genetic fusions of heat-labile (LT) and heat-stable (ST) toxoids of porcine enterotoxigenic *Escherichia coli* elicit neutralizing anti-LT and anti-STa antibodies." Infection and Immunity, 78(1):316-25 (Jan. 2010, published online Oct. 26, 2009).

Written Opinion of the International Searching Authority for International Application No. PCT/IB2014/000267 (dated Nov. 14, 2014).

Altboum et al., "Genetic characterization and immunogenicity of *coli* surface antigen 4 from enterotoxigenic *Escherichia coli* when it is expressed in a Shigella live-vector strain," Infect Immun. 71(3):1352-1360 (2003).

Borgia et al., "Chemical synthesis of proteins," TIBTECH 18(6):243-251 (2000).

Garrett et al., "A conformational epitope in the N-terminus of the *Escherichia coli* heat-stable enterotoxins is involved in receptor-ligand interactions," Biochim Biophys Acta 1317(2):149-154 (1996).

Giannella R A, "Suckling mouse model for detection of heat-stable *Escherichia coli* enterotoxin: characteristics of the model," Infect Immun., 14(1):95-99 (1976).

Guarino et al., "T84 cell receptor binding and guanyl cyclase activation by *Escherichia coli* heat-stable toxin," Am J Physiol., 253:G775-780 (1987).

Jertborn et al., "Safety and immunogenicity of an oral inactivated enterotoxigenic *Escherichia coli* vaccine," Vaccine, 16(2-3):255-260 (1998).

Klipstein et al., "Protection in rats immunized with *Escherichia coli* heat-stable enterotoxin," Infect Immun, 34 (2):637-639 (1981).

Lockwood et al., "Development of a competitive enzyme-linked immunosorbent assay (ELISA) for *Escherichia coli* heat-stable enterotoxin (STa)," J Immunol Methods, 75(2):295-307 (1984).

(Continued)

*Primary Examiner* — Brian Gangle

(74) *Attorney, Agent, or Firm* — McDonnell Boehnen Hulbert & Berghoff LLP

(57) ABSTRACT

A mutant of an *E coli* heat-stable toxin (ST) having the following wild-type sequence: NSSNYCCELCCNPACT-GCY wherein the mutant comprises a mutation selected from the group consisting of: A14H, A14T and N12T.

20 Claims, 6 Drawing Sheets

Specification includes a Sequence Listing.

(56) References Cited

OTHER PUBLICATIONS

Rivera et al., "Genotypic and phenotypic characterization of enterotoxigenic *Escherichia coli* strains isolated from Peruvian children," J Clin Microbol., 48(9):3198-3203 (2010).
Sack et al., "Randomised, double-blind, safety and efficacy of a killed oral vaccine for enterotoxigenic *E. coli* diarrhoea of travellers to Guatemala and Mexico," Vaccine, 25(22):4392-400 (2007).
Taxt et al., "Characterization of immunological cross-reactivity between enterotoxigenic *Escherichia coli* heat-stable toxin and human guanylin and urogyanylin," Infection and Immunity, 82(6):38 (2014).

Figure 1: Structural model of STh.

Figure 2: T84 toxicity compared to STh antigenticity.

Figure 3. T84 toxicity compared to STh antigenticity.

Figure 4. STp antigenicity compared to STh antigenticity.

VACCINE

CROSS-REFERENCE TO RELATED APPLICATIONS

This application is a national stage application under 35 U.S.C. § 371 of International Application No. PCT/IB2014/000267, filed Feb. 20, 2014, which claims priority to U.S. Provisional Application No. 61/766,958, filed Feb. 20, 2013, U.S. Provisional Application No. 61/767,161, filed Feb. 20, 2013, U.S. Provisional Application No. 61/850,636, filed Feb. 20, 2013, and U.S. Provisional Application No. 61/886,242, filed Oct. 3, 2013, the disclosure of each of which are explicitly incorporated by reference herein in their entirety.

FIELD OF THE INVENTION

The present invention relates to vaccines against enterotoxigenic *Escherichia coli* (ETEC). More specifically, the present invention relates to mutants of the ETEC heat-stable enterotoxin that are suitable for use as vaccine components.

BACKGROUND TO THE INVENTION

Enterotoxigenic *Escherichia coli* (ETEC) is a Gram-negative bacterium that is responsible for between 280 million and 400 million episodes of diarrhoea, and approximately 380,000 deaths per year (Taxt et al. Infect Immun. 2010 May; 78(5):1824-31. Epub 2010 Mar. 15). Most of the victims are children of less than 5 years of age living in developing countries. In addition, ETEC is considered the most common cause of traveller's diarrhoea.

ETEC colonises the small intestine and is transmitted by the faecal-oral route. The bacteria adhere to the intestinal epithelium via characteristic colonisation factors (CFs). CFs are fimbriae or fibrillae-filamentous proteins that are presented on the bacterial surface. To date, 25 distinct ETEC CFs have been identified (Rivera et al., J Clin Microbiol. 2010 September; 48(9): 3198-3203).

Numerous attempts have been made at developing an ETEC vaccine but no broadly effective vaccines are available to protect humans against ETEC diarrhea. A killed whole-cell vaccine represents the most promising candidate to date (Jertborn et al. Vaccine 1998; 16:255-60, Sack et al. Vaccine, 2007 May 30; 25(22):4392-400. Epub 2007 Apr. 4). This comprises five ETEC strains that are co-administered with recombinant cholera toxin B subunit (CT-B). The five ETEC strains were selected to provide the most common CFs.

Enterotoxins known as Heat Stable (ST) and heat-labile (LT) toxins, in addition to CFs are virulence determinants in ETEC diarrhoea. Both toxins act by stimulating net secretion of ions and water by intestinal epithelial cells. This causes watery diarrhoea, which can lead to a cholera-like condition in the most extreme cases.

ST was identified as target for an ETEC vaccine in the early 1980s but, despite many attempts, no successful ST-based vaccine has been developed.

Three main problems underlie the difficulty in utilising ST as a vaccine component. First, the ST polypeptide is inherently toxic. Second, in its natural form, the ST polypeptide is non-immunogenic. Finally, ST closely resembles the endogenous polypeptides guanylin and uroguanylin, which raises the possibility that anti-heat-stable toxin antibodies may cross-react, and cause autoimmune disorders in vaccinees.

Several ST mutants have been reported to reduce toxicity (Taxt, A. et al. *Infect. Immun.* 78, 1824-1831 (2010) and Liu, M. et al. *Toxins* 3, 1146-1162 (2011). However, as ST is a small polypeptide, most mutants with reduced toxicity also have reduced immunogenicity.

The problem of providing a heat-stable toxin mutant that exhibits both reduced toxicity and specific immunogenicity remains a significant challenge. Despite numerous attempts, no successful heat-stable toxin vaccine component has been developed that elicits a neutralising and protective immune response.

SUMMARY OF THE INVENTION

It is an object of the present invention to provide heat-stable toxin mutants that can be used as ETEC vaccine components. Specifically, it is intended to provide mutants of heat-stable enterotoxin (ST) that exhibit no or very low toxicity and are able to elicit a neutralizing, specific immune response when coupled to a suitable carrier.

To address this problem, a systematic screen of all 361 possible single point mutants human ST (STh) has been performed. The mutants were expressed with a signal sequence to direct the proteins for secretion from the host cell and expression was carried out using an *E. coli* lab strain. This experimental model effectively mimics native ST production by ETEC.

The toxicity of the ST mutant library was assessed using filtered culture supernatants in the GC-C receptor cell assay.

Antigenicity was screened as a proxy for immunogenicity. Antigenicity was assessed using a competitive, heat-stable toxin ELISA to measure the extent to which polyclonal antibodies raised in rabbits against wild-type heat-stable toxin bind to the recombinantly expressed heat-stable toxin mutants.

Using this systematic screening approach, ST mutants for use in an ETEC vaccine have been identified. Such mutants exhibit both reduced toxicity and retained/improved antigenicity.

According to a first aspect of the invention there is provided a mutant of an *E. coli* heat-stable toxin (ST) having the following wild-type sequence:

NSSNYCCELCCNPACTGCY (SEQ ID NO: 1)

wherein the mutant comprises a mutation selected from Table 1 or 2.

The mutant *E. coli* heat-stable toxin (ST) may comprise two mutations selected from Table 1 or 2.

According to another aspect of the present invention there is provided a mutant of an *E. coli* heat-stable toxin (ST) comprising the following wild-type sequence:

NSSNYCCELCCNPACTGCY (SEQ ID NO: 1)

wherein the mutant comprises a mutation selected from the group consisting of: A14H, A14T and N12T.

Preferably the mutant comprises an A14H mutation.

In another embodiment, the mutant has two mutations wherein the first mutation is A14H and the second mutation is selected from N12K, N12V, N12T, N12E, N12R, N12S, N12G, N12A, N12W, N12Q, L9G, L9S, L9A, L9E, L9P, L9D, L9R, P13A, P13F, P13E, C11H, E8R and E8K.

In another embodiment, the mutant has two mutations wherein the first mutation is A14H and the second mutation is selected from N12K, N12V, N12T, N12E, N12R, N12S, N12G, N12A, N12W and N12Q.

In another embodiment, the mutant has two mutations wherein the first mutation is N12T and the second mutation is selected from A14H, A14Q, A14R, A14T, A14E, A14I, A14L, A14K, A14W, A14N, A14M, A14D, A14F, A14V, A14Y, A14C, L9G, L9S, L9A, L9E, L9P, L9D, L9R, P13A, P13F, P13E, C11H, E8R and E8K.

In another embodiment, the mutant has two mutations wherein the first mutation is A14T and the second mutation is selected from N12K, N12V, N12T, N12E, N12R, N12S, N12G, N12A, N12W, N12Q, L9G, L9S, L9A, L9E, L9P, L9D, L9R, P13A, P13F, P13E, C11H, E8R and E8K.

In a preferred embodiment the mutant has the following mutations: A14H and N12K.

In another preferred embodiment the mutant has a single A14H point mutation.

The mutant according to the present invention may further comprises a T16A mutation.

According to another aspect of the present invention there is provided a mutant of an *E. coli* heat-stable toxin (ST) having the following wild-type sequence:

NSSNYCCELCCNPACTGCY (SEQ ID NO:1)

wherein the mutant comprises a mutation at position T16 in combination with a mutation at position N12 and/or A14.

The mutant may have a T16A mutation in combination with a mutation selected from A14H, A14Q, A14R, A14T, A14E, A14I, A14L, A14K, A14W, A14N, A14M, A14D, A14F, A14V and A14Y.

In another embodiment the mutant may have a T16A mutation in combination with a mutation selected from N12K, N12V, N12T, N12E, N12R, N12S, N12G, N12A, N12W and N12Q.

In another embodiment the mutant may have a T16A mutation in combination with a mutation selected from N12K, N12V, N12T, N12E, N12R, N12S, N12G, N12A, N12W and N12Q, and further in combination with a mutant selected from A14H, A14Q, A14R, A14T, A14E, A14I, A14L, A14K, A14W, A14N, A14M, A14D, A14F, A14V and A14Y.

In one embodiment the mutant has the following mutations: A14H and T16A.

In another embodiment the mutant has the following mutations: N12K and T16A.

According to another aspect of the present invention there is provided a mutant of an *E. coli* heat-stable toxin (ST) comprising the following wild-type sequence:

NTFYCCELCCNPACAGCY (SEQ ID NO: 2)

wherein the mutant comprises a mutation selected from the group consisting of: A13H, A13T and N11T.

Preferably the mutant comprises a A13H mutation.

In another embodiment, the mutant has two mutations wherein the first mutation is A13H and the second mutation is selected from N11K, N11V, N11T, N11E, N11R, N11S, N11G, N11A, N11W, N11Q, L8G, L8S, L8A, L8E, L8P, L8D, L8R, P12A, P12F, P12E, C10H, E7R and E7K.

In another embodiment, the mutant has two mutations wherein the first mutation is A13H and the second mutation is selected from N11K, N11V, N11T, N11A, N11R, N11S, N11G, N11A, N11W and N11Q.

In one embodiment, the mutant has two mutations wherein the first mutation is N11T and the second mutation is selected from A13H, A13Q, A13R, A13T, A13E, A13I, A13L, A13K, A13W, A13N, A13M, A13D, A13F, A13V, A13Y, A13C, L8G, L8S, L8A, L8E, L8P, L8D, L8R, P12A, P12F, P12E, C10H, E7R and E7K.

In another embodiment, the mutant has two mutations wherein the first mutation is N11T and the second mutation is selected from A13H, A13Q, A13R, A13T, A13E, A13I, A13L, A13K, A13W, A13N, A13M, A13D, A13F, A13V and A13Y.

In another embodiment, the mutant has two mutations wherein the first mutation is A13T and the second mutation is selected from N11K, N11V, N11T, N11A, N11R, N11S, N11G, N11A, N11W, N11Q, L8G, L8S, L8A, L8E, L8P, L8D, L8R, P12A, P12F, P12E, C10H, E7R and E7K.

In a preferred embodiment the mutant has the following mutations: A13H and N11K.

In another preferred embodiment the mutant has a single A13H point mutation.

In a very preferred embodiment, ST mutant of the invention is coupled to a carrier, for example, bovine serum albumin.

ST mutants can be coupled to carrier proteins to create molecules with improved immunogenic properties. Suitable carrier proteins are well known to those skilled in the art. Coupling to a carrier protein can be accomplished using, for example, genetic and chemical conjugation approaches.

According to another aspect of the present invention there is provided an isolated nucleic acid that encodes the ST mutant of the invention.

According to another aspect of the present invention there is provided a vector comprising the nucleic acid of the invention.

According to another aspect of the present invention there is provided a host cell comprising the vector of the invention.

Host cells of the invention include prokaryotic and eukaryotic cells. Suitable prokaryotic host cells include bacteria, for example *E. coli*. Suitable eukaryotic cells include yeast, insect cells (e.g. Sf9 cells) and mammalian cell lines.

According to another aspect of the present invention there is provided an antibody that is immunospecific for the ST mutant.

According to another aspect of the present invention there is provided a vaccine composition comprising the ST mutant, nucleic acid or vector of the invention, and a pharmaceutically acceptable carrier or excipient.

According to another aspect of the present invention there is provided an ST mutant, nucleic acid or vector of the invention for use in treating or preventing *E. coli* infection.

According to another aspect of the present invention there is provided an ST mutant, nucleic acid or vector of the invention for use in treating or preventing traveller's diarrhoea.

According to another aspect of the present invention there is provided a method for treating or preventing *E. coli* infection comprising administering an ST mutant, a nucleic acid or a vector of the invention to a patient in need of the same.

According to another aspect of the present invention there is provided a mutant of an *E. coli* heat-stable toxin (ST) comprising the following wild-type sequence:

NSSNYCCELCCNPACTGCY (SEQ ID NO: 1)

wherein the mutant comprises an N12K mutation in combination with a mutation selected from the group consisting of A14H, A14Q, A14R, A14T, A14E, A14I, A14L, A14K, A14W, A14N, A14M, A14D, A14F, A14V, A14Y, A14C, L9G, L9S, L9A, L9E, L9P, L9D, L9R, P13A, P13F, P13E, C11H, E8R and E8K.

According to another aspect of the present invention there is provided a mutant of an *E. coli* heat-stable toxin (ST) comprising the following wild-type sequence:

NSSNYCCELCCNPACTGCY (SEQ ID NO: 1)

wherein the mutant comprises N11K mutation in combination with a mutation selected from the group consisting of A13H, A13Q, A13R, A13T, A13E, A13I, A13L, A13K, A13W, A13N, A13M, A13D, A13F, A13V, A13Y, A13C, L8G, L8S, L8A, L8E, L8P, L8D, L8R, P12A, P12F, P12E, C10H, E7R and E7K.

Figure 1:
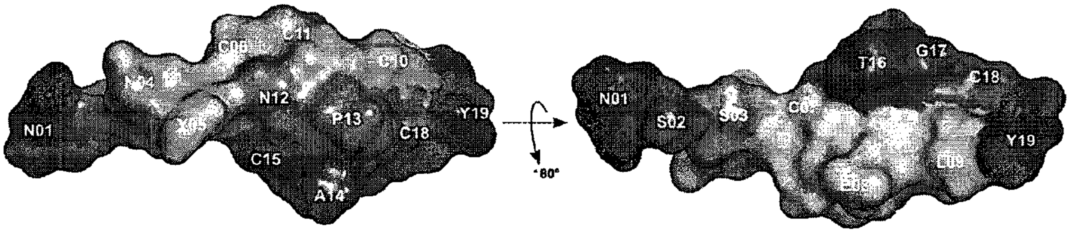
FIG. 1. Structural model of STh. Amino acids are labelled and coloured grayscale gradient from the N-terminus to the C-terminus. Two views of the structure are shown, rotated 180° along the x axis in relation to each other.

Table 1. STh toxoid candidates. All toxoid candidates that had toxoidicities of one hundred or more are shown above the double line, and the best toxoid candidate for each position that had a maximum toxoidicity higher than ten are shown below. Both toxicities and antigenicities are relative to native STh. [1]Antigenicity was out of the quantitative range of the assay, and was conservatively set to 2 times wild-type level. [2]Mutants that did not display detectable toxicity in the T84 cell GC-C receptor assay were set to the detection limit of the assay which was 0.0014.

Table 2. All STh mutants ranked by toxoidicity

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis (1989) Molecular Cloning: A Laboratory Manual, Second Edition, Books 1-3, Cold Spring Harbor Laboratory Press; Ausubel, F. M. et al. (1995 and periodic supplements) Current Protocols in Molecular Biology, Ch. 9, 13, and 16, John Wiley & Sons, New York, N.Y.; B. Roe, J. Crabtree, and A. Kahn (1996) DNA Isolation and Sequencing: Essential Techniques, John Wiley & Sons; J. M. Polak and James O'D. McGee (1990) In Situ Hybridization: Principles and Practice; Oxford University Press; M. J. Gait (ed.) (1984) Oligonucleotide Synthesis: A Practical Approach, IRL Press; and, D. M. J. Lilley and J. E. Dahlberg (1992) Methods of Enzymology: DNA Structure Part A: Synthesis and Physical Analysis of DNA Methods in Enzymology, Academic Press. Each of these general texts is herein incorporated by reference.

Enterotoxigenic *Escherichia coli* (ETEC) Toxins

ETEC secretes two essential virulence factors, the heat-labile and/or heat-stable enterotoxins. Both toxins act by stimulating net secretion of ions and water by intestinal epithelial cells. This causes watery diarrhoea, which can lead to a cholera-like condition in the most extreme cases.

Heat-Labile Toxin

ETEC heat-labile toxin is an 84 kDa oligotoxin that is related to cholera toxin in structure and mechanism. It stimulates increased concentrations of cAMP in intestinal epithelial cells. This results in a net secretion of chloride ions and water, causing watery diarrhoea.

Heat-Stable Toxin

Two distinct ETEC heat-stable toxins have been identified, STa/STI and STb/STII. These proteins are structurally, functionally and immunologically unrelated. STa/STI is the subject of this invention and is referred to herein as ST.

Epidemiological studies strongly indicate that ETEC strains which secrete ST contributes more to the diarrheal disease burden of children of developing countries than do ETEC strains that only produce LT.

The genes encoding ETEC ST proteins are harboured on transmissible plasmids. The ST proteins are expressed as 72 amino acid immature pre-pro-peptides. Residues 1-19 of the pre-pro-peptide constitute a signal peptide that targets the immature protein for secretion across the inner membrane via the Sec machinery. The pro-peptide is then processed to the mature form with translocation across the outer membrane.

The mature ST is an approximately 2 kDa polypeptide. Two ST variants are known:

1. STh (also known as STIb and STaII): a 19 amino acid polypeptide isolated from ETEC strains infecting humans;
2. STp (also known as STIa and STaI): an 18 amino acid polypeptide isolated from both ETEC strains infecting humans and animals.

The mature STh polypeptide (corresponding to residues 54-72 of the immature pre-pro-peptide) has the amino acid sequence:

NSSNYCCELCCNPACTGCY (SEQ ID NO: 1)

The mature STp polypeptide (corresponding to residues 55-72 of the immature pre-pro-peptide) has the amino acid sequence:

NTFYCCELCCNPACAGCY (SEQ ID NO: 2)

For the purposes of the present invention, unless stated otherwise, the ST amino acid residues and mutants will be numbered according to the relevant mature polypeptide sequences.

Both ST variants are non-immunogenic in their natural forms.

Mature STh and STp contain three intramolecular disulfide bonds arranged in a 1-4/2-5/3-6 pattern (here the numbering corresponds to the order of cysteine residues in the mature polypeptide). The periplasmic disulfide isomerase (DsbA) is required for disulfide bond formation.

ST binds to and activates the guanylate cyclase C (GC-C) receptor by mimicking the endogenous ligands, guanylin and uroguanylin. ST binding results in increased concentrations of intracellular messenger cyclic GMP (cGMP). This causes decreased absorption of sodium and chloride ions, and increased secretion of bicarbonate and chloride ions, which ultimately results in diarrhoea.

ETEC ST polypeptides are structurally similar to both guanylin and uroguanylin. Both guanylin and uroguanylin contain only two disulfide bonds and interconvert between two distinct conformations. The three ST disulfide bonds appear to lock the ST polypeptide into a conformation that resembles the active conformation of guanylin and uroguanylin. The two ST disulfide bonds that are common with guanylin and uroguanylin are essential for activity. Mutation of any ST cysteine that corresponds to one of these disulfide bonds abolishes or dramatically reduces toxicity.

The section of ST from the first to last cysteine are referred to as the toxic domain.

ETEC Heat-Stable Toxin Mutants

The present invention provides a mutant of an *E. coli* heat-stable toxin (ST) comprising the following wild-type sequence:

NSSNYCCELCCNPACTGCY (SEQ ID NO.: 1)

wherein the mutant comprises a mutation shown in Table 1 or Table 2.

The present invention furthers a mutant of an *E. coli* heat-stable toxin (ST) having the following wild-type sequence:

NSSNYCCELCCNPACTGCY (SEQ ID NO.: 1)

wherein the mutant comprises a mutation selected from the group consisting of: A14H, A14T and N12T.

Preferably the mutant comprises an A14H mutation.

The mutant ST may comprise more than one mutation. For example, the mutant may have mutant has the following mutations: A14H and N12K; or A14H and N12IT; or A14H and N12I.

The present invention also provides a mutant of an *E. coli* heat-stable toxin (ST) having the following wild-type sequence:

NTFYCCELCCNPACAGCY (SEQ ID NO: 2)

wherein the mutant comprises a mutation selected from the group consisting of: A13H, A13T and N11T.

Preferably the mutant comprises an: A13H mutation.

The mutant ST may comprise more than one mutation. For example, the mutant may have the following mutations: A13H and N11K; or A13H and N11IT; or A13H and N11I.

It is envisaged that additional mutations may be made in the mutants of the present invention to create, for example, double or triple mutants. Such additional mutations may further improve the properties of the ST mutants of the present invention, for example by reducing toxicity and increasing ST-specific immunogenicity.

The mutants of the present invention can be obtained by methods well known in the art. Various techniques for the chemical synthesis of peptides are reviewed by Borgia and Fields, 2000, TibTech 18: 243-251, and are described in detail in the references contained therein.

Conjugates/Carriers

The present invention also provides conjugates wherein a mutant of the present invention is coupled to a carrier.

Carriers of the present invention may be useful in increasing the immunogenicity of ST. Numerous carriers are known in the art.

Suitable carriers include, but are not limited to, immunoglobulin G (IgG), bovine serum albumin (BSA), heat-labile enterotoxin A-subunit (LT-A), heat-labile enterotoxin B-subunit (LT-B), cholera toxin B-subunit (CT-B), the outer membrane protein OmpC, the ZZ fragment of *Staphylococcus aureus* protein A, the major subunit ClpG of *E. coli* CS31A fimbriae, *Salmonella* flagellin and green fluorescent protein (GFP).

Conjugation with certain carriers, for example LT-B and CT-B, may advantageously provide immune protection against both ETEC ST and LT.

It is envisaged that coupling may be carried out by a range of techniques known in the art, including chemical conjugation, genetic fusion or direct protein synthesis.

Chemical conjugation approaches include the coupling of pre-formed proteins by using a cross-linking agent.

Genetic fusion includes the approach of linking a mutant of the present invention to a carrier through the polypeptide backbone of each protein to create a fusion protein. This may be achieved by expression of a gene encoding such a fusion protein. The proteins may be coupled at the N- or C-termini of either protein. Alternatively, one protein may be inserted into another protein in such a manner that the structures and functions of both proteins are substantially not altered, for example by incorporation into a loop region. Proteins may be coupled directly or via polypeptide linkers.

Finally, the mutants may be expressed by live vaccine vectors, such as attenuated *Shigella* strains (Altboum et al. Infect Immun. 2003 March; 71(3):1352-60).

Peptide Variants, Derivatives and Fragments

The present invention also encompasses variants and derivatives of the mutant ST proteins disclosed herein.

Terms "variant" or "derivative" in relation to amino acid sequences of the present invention includes any substitution of, variation of, modification of, replacement of, deletion of or addition of one (or more) amino acids from or to the sequence, providing the resultant amino acid sequence preferably has substantially the same therapeutic activity.

Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other.

| | | |
|---|---|---|
| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

Polynucleotides, Vectors and Host Cells

The present invention also provides polynucleotides encoding the *E. coli* heat-stable toxin mutants of the invention.

It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the field of the invention.

Such modifications may be carried out in order to enhance the in vivo activity or life span of polynucleotides.

Polynucleotides of the invention can be incorporated into a recombinant replicable vector. The vector may be used to replicate the nucleic acid in a compatible host cell.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Control sequences operably linked to sequences encoding the mutant of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

Vectors of the invention may be transformed or transfected into a suitable host cell so as to provide for expression of an ST mutant of the invention. This process may comprise culturing a host cell transformed with an expression vector as described above under conditions to provide for expression by the vector of a coding sequence encoding the mutant, and optionally recovering the expressed protein.

The polynucleotide or vector of the invention may be administered to a subject such that the mutant ST peptide is expressed in-vivo. Examples of such vectors include, for example, plasmids and viral vectors.

Examples of viral vectors include retroviral vectors, Murine Leukemia Virus (MLV) vectors, adenovirus vectors, pox viral vectors and vaccinia viral vectors. Examples or retroviral vectors include murine leukemia virus (MLV), human immunodeficiency virus (HIV-1), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al., 1997, "retroviruses", Cold Spring Harbour Laboratory Press Eds: J M Coffin, SM Hughes, HE Varmus pp 758-763.

Antibodies

The present invention also provides a polyclonal or monoclonal antibody that is immunospecific for an ST mutant disclosed herein.

As used herein, the term "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term "antibody", as used herein, also includes antibody fragments which retain their binding activity for a target antigen, either produced by the modification of whole antibodies or synthesised de novo using recombinant DNA methodologies. Antibody fragments encompassed by the use of the term "antibody" include, but are not limited to, Fab, Fab', F (ab')2, Fv, scFv, dsFv diabody and Fd fragments. Furthermore, the antibodies and fragments thereof may be humanised antibodies.

ST mutants according to the invention may be used directly as immunogens to generate antisera and monoclonal antibodies. The invention thus provides a method for inducing antigen specific immunoglobulin production comprising the steps of:

a) immunising an animal or human with a mutant according to the present invention; and b) recovering immunoglobulin(s) specific for a region of the mutant from the serum of the animal.

The animals used for antibody production may be any animals normally employed for the purpose, particularly mammals. Especially indicated are mice, rats, guinea pigs and rabbits.

Immunisation is carried out according to established techniques (see "Antibodies, A Laboratory Manual" by E. Harlow and D. Lane (1988) Cold Spring Harbor, U.S.A.).

More particularly, the mutant of the present invention can be used to produce both polyclonal and monoclonal antibodies.

If polyclonal antibodies are desired, a selected mammal (e.g. mouse, rabbit, goat, horse, etc.) is immunised. Serum from the immunised animal is collected and treated according to known procedures. If the serum contains polyclonal antibodies to other antigens, the polyclonal antibodies can be purified by immunoaffinity chromatography. Techniques for producing and processing polyclonal antisera are known in the art.

Monoclonal antibodies directed against antigens used in the invention can also be readily produced by those skilled in the art. The general methodology for making monoclonal antibodies by hybridomas is well known. Immortal antibody-producing cell lines can be created by cell fusion and also by other techniques such as direct transformation of B-lymphocytes with oncogenic DNA or transfection with Epstein-Barr virus. Panels of monoclonal antibodies produced against antigens can be screened for various properties, for example for isotype and epitope affinity.

An alternative technique involves screening phage display libraries where, for example, the phage express scFv fragments on the surface of their coat with a large variety of complementary determining regions (CDRs). This technique is well known in the art.

Antibodies, both monoclonal and polyclonal, which are directed against antigens are particularly useful in diagnosis, and those which are neutralising are useful in passive immunotherapy. Monoclonal antibodies in particular may be used to raise anti-idiotype antibodies. Anti-idiotype antibodies are immunoglobulins which carry an "internal image" of the antigen of the infectious agent against which protection is desired.

Techniques for raising anti-idiotype antibodies are known in the art. These anti-idiotype antibodies may also be useful for treatment, as well as for an elucidation of the immunogenic regions of antigens.

Vaccine Compositions

The present invention also provides a vaccine composition comprising an ST mutant or nucleic acid of the invention, and a pharmaceutically acceptable carrier or excipient.

The preparation of vaccines which contain an immunogenic polypeptide(s)/polynucleotide(s) as active ingredient(s), is known to those skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

An adjuvant is any pharmacologically acceptable substance which enhances the immune response to an antigen or allergen. Thus, a $T_h1$-inducing adjuvant enhances the response of $T_h1$ cells to an antigen or allergen.

Examples of adjuvants which may be effective include, but are not limited to, aluminium hydroxide, tyrosine and derivatives thereof, N-acetyl-muramyl-L-threonyl-D-isoglutamine (Thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium phosphate, aluminium potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), a mixture of Amphigen and Alhydrogel, tyrosine and derivatives thereof, and calcium phosphate are used.

Adjuvants that interact with toll-like receptors on phagocytic, and endocyte and/or antigen presenting cells, for example, but not limited to toll-like receptors 2 and/or 4 and/or 9 may be used. Examples of these adjuvants are, but not limited to, the $T_h1$ inducing adjuvant monophosphoryl lipid A (MPL, see U.S. Pat. Nos. 4,912,094 and 4,987,237), and its derivatives and synthetic analogues, and the CpG DNA motif and its derivatives and analogues.

The proportion of immunogen and adjuvant can be varied over a broad range so long as both are present in effective amounts. For example, aluminium hydroxide can be present in an amount of about 0.5% of the vaccine mixture ($Al_2O_3$ basis).

The effectiveness of an adjuvant may be determined by measuring the amount of antibodies directed against an immunogenic agent resulting from administration of this agent in vaccines which are also comprised of the various adjuvants.

The vaccines are conventionally administered parenterally, by injection, for example either intradermally, subcutaneously or intramuscularly. Additional formulations which are suitable for other modes of administration include suppositories and oral formulations.

For suppositories, traditional binders and carriers may include, for example, polyalkylene glycols or triglycerides.

Oral formulations include such normally employed excipients as, for example, pharmaceutical grades of mannitol, lactose, starch, magnesium stearate, sodium saccharine, cellulose, sodium bicarbonate, magnesium carbonate, and the like. These compositions take the form of solutions, suspensions, tablets, pills, capsules, sustained release formulations or powders and may contain, for example, 10% to 95% of active ingredient, preferably 25% to 70%. Where the vaccine composition is lyophilised, the lyophilised material may be reconstituted prior to administration, for example as a suspension. Reconstitution is preferably effected in buffer.

Dosage and Administration of Vaccines

The vaccines are administered in a manner compatible with the dosage formulation, and in such amount as will be prophylactically and/or therapeutically effective.

A prophylactic vaccine is one which prevents disease. The quantity to be administered may depend on the subject to be treated and the capacity of the subject's immune system to synthesise antibodies.

Precise amounts of active ingredient required to be administered may depend on the judgement of the practitioner and may be peculiar to each subject.

The vaccine may be given in a single dose schedule or in a multiple dose schedule. A multiple dose schedule is one in which a primary course of vaccination may be with 1-10 separate doses followed by other doses given at subsequent time intervals required to maintain and/or reinforce the immune response, for example, at 2 to 4 weeks after the first dose, and if needed, a subsequent dose(s) after several months. The dosage regimen will also, at least in part, be determined by the need of the individual and be dependent upon the judgement of the practitioner.

In addition, the vaccine containing the antigen(s) may be administered in conjunction with other immunoregulatory agents, for example immunoglobulins.

It is to be appreciated that all references herein to treatment include curative, palliative and prophylactic treatment. The treatment of mammals is particularly preferred. Both human and veterinary treatments are within the scope of the present invention.

Methods of Screening Mutants

The present invention also provides a method for screening for mutants of an *E. coli* heat-stable toxin that have reduced toxicity and either maintained or increased specific antigenicity and, it is expected, for some mutants immunogenicity.

The method of the invention relates to analysing a library of mutants of an *E. coli* heat-stable toxin for toxoidicity. The term "toxoid" is defined as a mutant of ST that exhibits no or very low toxicity, and which is able to elicit an effective, ST-specific immune response when coupled to a suitable carrier.

The method of the invention includes methods of screening for mutants of an *E. coli* heat-stable toxin that are present in culture filtrates. One challenge when measuring toxicity in culture filtrates is that it is a product of intrinsic toxicity (toxicity per mole) and the concentration of the ST mutant. The same is true for antigenicity. Hence, a decrease in toxicity or antigenicity, as compared to native ST, may be due to a lower ST concentration, decrease in intrinsic toxicity/antigenicity, or a combination of the two. Accurately measuring ST mutant concentration in culture filtrates is challenging.

The first step in circumventing the problem of measuring intrinsic toxicity and antigenicity is to measure toxicity and antigenicity for the ST mutants in the same supernatant and relative to native ST. This allows us to describe changes in toxicity and antigenicity in mutant culture filtrates. The second step is then to divide the change in antigenicity by the change in toxicity for each mutant. If the same culture filtrate has been used to measure toxicity and antigenicity this allows us to eliminate the effects of the concentration. This measure is defined as "toxoidicity":

$$\text{toxoidicity} = \frac{A_r}{T_r} = \frac{A_i \times c}{T_i \times c} = \frac{A_i}{T_i}$$

where c is the concentration, $A_r$ is the relative antigenicity of the culture filtrate, $T_r$ is the relative toxicity of the culture filtrate, $A_i$ is the intrinsic antigenicity and $T_i$ is the intrinsic toxicity. Good toxoid candidates will have a high toxoidicity.

In one embodiment, a library of mutants of an ST gene incorporated into a suitable expression vector may be created by any of the methods that are well-known in the art. Such methods include site-directed mutagenesis, random mutagenesis and de novo DNA synthesis.

The proteins encoded by the library may be produced by incorporation of the vectors into suitable host cells, culturing the host cells under conditions that permit the expression of the mutants by the host cell and isolation of the mutant proteins. Numerous vectors and host cells are known in the art, as described above, and suitable vectors and host cells can be readily selected by the skilled person. Preferred host cells for the present invention are prokaryotic host cells, particularly *E. coli*. It is a preferred feature of the invention to construct the mutant library and conduct the expression in such a manner that the mutant proteins are secreted from the host cells into the culture medium. This may be accomplished, for example, by incorporating a secretion signal sequence that is operably linked to the gene in the expression vector.

Mutants that exhibit reduced toxicity and increased specific immunogenicity (i.e. toxoid candidates) may be determined by carrying out toxicity and antigenicity assays on the expressed proteins of the mutant library. Toxoid candidates may be identified by calculating the toxoidicity as defined above.

Suitable assays for analysing the toxicity of the ST mutants include the GC-C receptor cell assay (PMID: 2892417; Guarino et al., Am J Physiol. 1987 December; 253(6 Pt 1):G775-80), the suckling mouse assay (PMID: 780280; Giannella, Infect Immun. 1976 July; 14(1):95-9) and the ligated gut loop assay (PMID:7030964; Klipstein et al., Infect Immun. 1981 November; 34(2):637-9). These methods are well known in the art.

Directly testing mutant immunogenicity would require purifying all possible mutants and individually coupling the purified proteins to carrier proteins. This is not feasible for large libraries. As an alternative, it is possible to screen antigenicity as a proxy for immunogenicity. Suitable assays for determining antigenicity include ELISA-based methods, for example competitive ELISA methods. In one embodiment, antigenicity may be assessed using a competitive, heat-stable toxin ELISA to measure the affinity of antibodies raised against wild-type heat-stable toxin for the recombinantly expressed heat-stable toxin mutants.

Examples

Methods

Generation and Expression of ST Mutant Library

The sta3 gene from enterotoxigenic *E. coli* strain H10407, encoding STh, was cloned into the pBAD-TOPO vector (Invitrogen). The resulting pBAD-STh vector contains the araBAD promoter, which allows tuneable expression by induction with 0.000002% to 0.2% arabinose. Mature ST was released into the culture supernatant when cells were induced at arabinose levels above 0.002%. Optimal expression was achieved with 0.2% arabinose.

The ST mutant library was expressed in batches of 19 ST mutants including 3 wild-type ST cultures as controls. Culture supernatants were isolated by centrifugation and were then filtered (0.2 μm filter). Supernatants were stored at −80° C.

Competitive ST ELISA

Competitive STh ELISA was performed as previously described (PMID: 6520401; Lockwood and Robertson, J Immunol Methods. 1984 Dec. 31; 75(2):295-307) with minor modifications. A U-shaped microtiter plate (Linbro, Fisher Scientific, Göteborg, Sweden) was coated with STh-ovalbumin conjugate diluted in ELISA buffer (NaCl 128 mM, KCl 2.68 mM, $KH_2PO_4$ 1.47 mM, $Na_2HPO_4$ 8.10 mM; pH 7.0-7.2). The plate was covered with plate sealer and incubated overnight at 37° C. Contents of the wells were discarded by inversion. Additional protein binding sites were blocked by incubating with ovalbumin 1% (w/v) (Sigma-Aldrich) diluted in ELISA buffer. After incubation for 1 h at 37° C., wells were emptied and washed three times with wash buffer (ELISA buffer containing ovalbumin 0.05% (w/v) and Tween-20 0.05% (v/v)). 75 μL of samples containing STh and 75 μL of diluted antisera (Protein-A purified rabbit anti-STa kindly supplied by John D. Clements; Department of Microbiology and Immunology, Tulane University, New Orleans, USA) were added. Both dilutions were done in ELISA buffer containing ovalbumin 0.05% (w/v). Appropriate dilutions and concentrations of reagents were determined by checkerboard titrations. The plate was incubated for 2 h at 37° C., in a rotary incubator shaker (Infors HT, Bottmingen/Basel Switzerland) at 180 rpm. Wells were emptied and washed three times with wash buffer. 100 μL of anti-Rabbit IgG Alkaline Phosphatase Conjugate developed in goat (Sigma-Aldrich) diluted 1:400 in ELISA buffer with ovalbumin 0.05% (w/v) were add and incubated with not shaking for 1 h at 37° C. Wells were emptied and washed three times with wash buffer followed by addition of 100 μL of 4-Nitrophenyl phosphate disodium salt hexahydrate at 1 mg/mL in diethanolamine buffer (diethanolamine 9.7% (v/v), $MgCl_2 \times 6H_2O$ 0.49 mM; pH 9.8). After incubation for 30 min, the reaction was stopped with 50 μL 2N NaOH (VWR international) in each well. The absorbance was read in an automatic plate reader at 405 nm (FLUOstar OPTIMA; BMG Labtech, Germany). All samples were measured in triplicate.

GC-C Receptor T-84 Cell Assay

T-84 cells were seeded and cultured in each well of a 24 well plate. After removing the Dulbecco's modified Eagle's medium (DMEM:F12 (1:1) Lonza Walkersville, Inc.), cells were washed 3 times with 0.5 mL DMEM. Cells were incubated with 0.25 mL DMEM containing 1 mM 3-isobutyl-1-methylxanthine (IBMX) for 10 min at 37° C. 0.1 mL of sample (culture filtrate) was added to each well and incubated for 60 min at 37° C. Following incubation, the reaction medium was aspirated, and the cells were lysed with 0.1 mM HCl at room temperature for 20 min. The lysates were centrifuged at top speed for 10 min and the cGMP levels were measured in control- and agonist-stimulated cells with a direct cGMP enzyme immunoassay kit (Enzo Life Sciences, Inc.) according to the manufacturer's instructions.

The culture filtrate of each mutant was added to the T-84 cells in duplicate, and a serial dilution of culture filtrates with recombinantly expressed native ST was used to generate a standard curve.

Screen for Toxicity and Antigenicity

Toxicity measured in culture filtrates is a product of intrinsic toxicity (toxicity per mol) and the concentration of the ST mutant. The same is true for antigenicity. Hence, a decrease in toxicity or antigenicity, as compared to native ST, may be due to a lower concentration, decrease in intrinsic toxicity/antigenicity, or a combination of the two. Since we have no method for accurately measuring ST (mutant) concentrations in culture filtrates, we are not able to directly measure intrinsic toxicities and antigenicities for the ST mutants.

To circumvent this problem we measure toxicity and antigenicity for the ST mutants relative to native ST. This allows us to describe changes in toxicity and antigenicity in mutant culture filtrates. Next, we divide the change in antigenicity by the change in toxicity for each mutant. If the same culture filtrate has been used to measure toxicity and antigenicity this allows us to eliminate the of the concentration. We define this measure as toxoidicity:

$$\text{toxoidicity} = \frac{A_r}{T_r} = \frac{A_i \times c}{T_i \times c} = \frac{A_i}{T_i}$$

where c is the concentration, $A_r$ is the relative antigenicity of the culture filtrate, $T_r$ is the relative toxicity of the culture filtrate, Ai is the intrinsic antigenicity, and $T_i$ is the intrinsic toxicity. Good toxoid candidates will have a high toxoidicity.

Purification of ST Mutants

*E. coli* BL21 cells were transformed with either of plasmids pUC19-STh [Zhang et al; PMID: 19858307], pUC19-STh-N12T, pUC19-STh-A14Q, pUC19-STh-A14T, and pUC19-STh-T16M, and were grown for 12h in 4AA medium (6 l). STh and STh mutants were purified from crude culture supernatants that were prepared by centrifugation followed by ultrafiltration by a procedure modified from Dreyfus et al [PMID:6358024]. Briefly, the crude culture supernatants were applied to an Amberlite XAD-2 column. The column was washed with distilled water, and ST was eluted with methanol/triflouroacetic acid (TFA) (volumes 99.9, 0.1, respectively), followed by 200 ml of methanol/water/TFA (volumes 80, 19.9, 0.1, respectively). The eluates were pooled, and the volume was reduced to 8-10 ml by evaporation, and subsequently applied to a Bio-Gel P-6 gel filtration column. The column was eluted with a 20 mM TrisHCl, 200 mM NaCl (pH 7.5) buffer at 4 C at a flow rate of 25 ml/h. The ST containing fractions were pooled and subjected to C18 reverse phase HPLC using a gradient of 30-85% methanol. The final sample is adjusted to pH 7.2-7.4 and stored at −20 C.

Chemical Conjugation of STh (Mutants) to Bovine Serum Albumin

STh (mutants) were chemically coupled to bovine serum albumin (BSA) using glutaraldehyde as described [Lockwood & Robertson; PMID:6520401].

Immunization of Mice

Mice were immunized intraperitoneally with 200 ng STh (mutant) conjugates in an equal volume of Freund's completed adjuvant (primary), and two boosters at the same dose (but with Freund's incomplete adjuvant) biweekly. Mice immunized with STh (mutant) conjugates developed anti-STh antibodies, but not the control mice.

Anti-ST Antibody Titration

Anti-ST IgG antibodies in serum of immunized mice were titrated. 10 ng ST-ovalbumin conjugates in 100 μl STa ELISA buffer (Zhang et al., 2010) were added to each well of a Costar plate (Corning Inc., Corning, N.Y.) and incubated for 1 h at 37° C. and followed by overnight at 4° C. After washing twice with PBST, blocked with non-fat milk (in PBST) at 37° C. for 1 h, plates were washed, had 100 μl serum (1:25 diluted in 1% milk-PBST) added to each well, and incubated 1 h at 37° C. After washing, each well had 100 μl HRP-conjugated goat-anti-mouse IgG antibodies added and incubated for 1 h at 37° C.; followed by washes and incubation with 100 μl TMB peroxidase substrate (KPL) for 20 min. Optical density (OD) was measured and antibody titers were calculated.

Neutralization Assay

Neutralization of STh by anti-STh mouse sera was tested by a cGMP EIA kit (Assay Design, Ann Arbor, Mich.) and T84-cells. T-84 cells were cultured as described above. 2 ng STh toxin (diluted in 150 μl DMEM/F12 medium) was incubated with 30 μl anti-sera (pooled from mice in the immunization group; diluted in 120 μl DMEM/F12 medium, in triplicate) at room temperature. After 1 h incubation, the mixture (150 μl STh toxin dilution and 150 μl of diluted anti-sera) was added to each well that had T-84 cells cultured in 700 μl culture medium, and the plate was further incubated at 37 C in 5% $CO_2$ for 2 hours. After another wash, the cells were lysed with 0.1M 11 HCl (200 μl per well), and then neutralized with 0.1 M NaOH. The cell lysates were collected with centrifugation at 660×g for 10 min at room temperature. Resultant supernatants were tested for intracellular cGMP levels by following the manufacturer's protocol.

Anti-ST Monoclonal Antibodies

The anti-STh mAb ST:G8 was kindly supplied by S. Visweswariah [Garrett & Visweswariah; PMID: 8950201]. The anti-STp mAbs clone 29, clone 30, and clone 31 were obtained from Fitzgerald Industries International.

Competitive STh ELISA Using Monoclonal Anti-ST Antibodies

ELISA-plates (Nunc Amino Immobilizer) were coated with STh-OvA conjugate in PBS, volume 100 μl per well (synthetic STh conjugated to OvA: For ST:G8 0.04 μl/well, for clone 29 and clone 30 0.01 μl/well). Plates were incubated overnight at 4 C. Subsequently, plates were emptied and blocked with PBS-T 1% OvA for 1h at 20° C. with shaking 180 rpm. After washing (3× with PBS-T) a volume of 60 μl of sample and 60 μl of primary antibody dilution was added to wells. Final dilutions of mAbs were as follows: ST:G8 1:6500, clone 29 1:16000, clone 30 1: 30000. Competitive incubation was performed for 90 minutes at 180 rpm, 20 C. Plates were then washed with 3×200 μl PBS-T and incubated at room-temperature for 1h with secondary antibody diluted in PBS-T 100 μl per well (anti-mouse dilution 1:400 for the ST:G8 ELISA, anti-mouse dilution 1:2000 for clone 29 and clone 30 ELISA). After renewed washing with 3×200 μl PBS-T, plates were developed with 100 μl developing buffer for 15-20 minutes. Developing was stopped by adding 50 μl NaOH 2M to each well, and OD was read at 405 nm with a Fluostar Optima plate reader.

For the clone 31 mAb a slightly different protocol was developed. ELISA plates (Nunc CovaLink) were coated with synthetic STp according to manufacturer's instructions. Briefly, 50 μl of PBS with STp was added to all wells. Subsequently a carbodiimide/EDC-solution was made by adding 1.84 mg BS3 to 5 mg EDC in 10 ml PBS, and 50 μl of this solution was added to all wells. Final concentration of STp was 0.5 μM in the coating solution. Plates were incubated overnight at 20° C. The ELISA was then performed with washing steps, blocking steps and development as described above. Prior to the competitive incubation step samples and antibody solutions were pre-mixed on a non-absorbing microtiter plate and subsequently transferred to the coating plate with a multi-channel pipette, thereby minimizing the time the coating plate was allowed to dry out. Final concentration of clone 31 primary antibody was 1:16000, secondary antibody was 1:500.

Results

All 361 mutant variants of ST were expressed in an *E. coli* TOP10 background, and culture filtrates were analysed for toxicity using the GC-C T-84 cell assay and antigenicity using the STh and STp competitive ELISA assays.

The assays have different detection limits: the detection limit for the STp ELISA is ~50-60 times diluted wild-type ST culture filtrates, the STh ELISA limit is ~400, whereas wild-type ST culture filtrates can be diluted ~700-750 times and still be detectable in the T-84 cell assay.

To aid in the interpretation of the results, a structural model of STh is shown in FIG. 1. The so-called toxic domain of STh is comprised by residues 6-18, and is identical to the STp residues 5-17, except for STh T16, which is replaced by A15 in STp. STh and STp also share the two tyrosines that flank the toxic domain (STh: Y05, Y19; STp: Y04, Y18), but differ in the N-terminus (STh: NSSN, STp: NTF). The residues in STh that have been proposed to interact with the guanylin cyclase C receptor are N12, P13, and A14, which correspond to the STp residues N11, P12, and A13.

Identification of ST Toxoid Candidates

Figure 2:
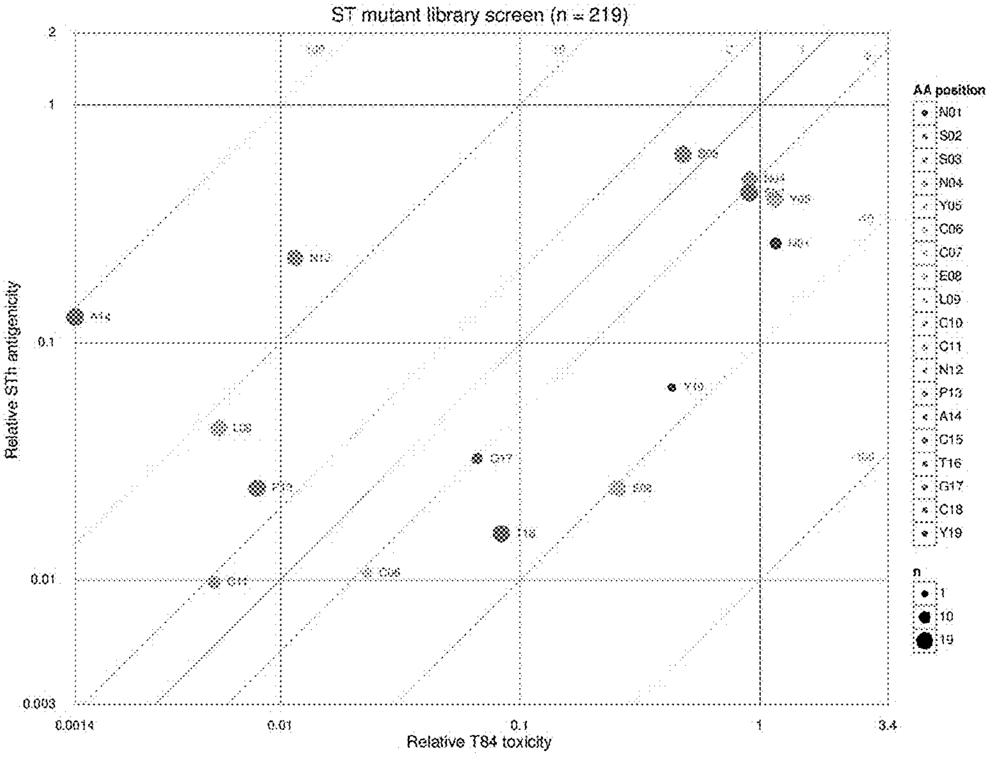
FIG. 2. T84 toxicity compared to STh antigenticity. The bubble chart shows the median relative T84 toxicity values for each amino acid position of STh (horizontal axis) plotted against the median relative STh antigenicity values (vertical axis). The axes are in logarithmic scale. The number of mutants (n) for each position that have both T84 toxicity and STh antigenicity values successfully determined are visualized by the bubble sizes. A total number of 219 mutants are represented in the chart. The bubbles are coded with different grayscale gradient according to amino acid position from the N- to C-terminus and are labelled. The diagonal dotted lines represent toxoidicities: the black line represents a toxoidicity of 1, the grey lines to the left represents toxoidicities of 2, 10, and 100, and the grey lines to the right toxoidicities of −2, −10 and −100.

The median effects on T84 toxicity and STh anigenicity for each amino acid position of STh are shown in FIG. 2. Note that the toxicity of mutants that did not have any detectable toxicity were set to the detection limit (0.0014) to ensure conservative assessments of effects on toxicity.

In the N-terminal positions N01, S02, S03, N04 and Y05, the median effects on both toxicity and antigenicity were small. In contrast, the toxic domain positions (16-18) and Y19 showed more dramatic effects on either toxicity, antigenicity, or both.

For positions C06, E08, T16, G17, and Y19, the median toxoidicities were negative, ranging from −2 (G17) to −10.5 (E08). This suggests that these positions (except G17) may form one or more epitopes recognized by the anti-STh antiserum. Note that residues E08 and T16 are on the opposite side of the so-called receptor interacting residues N12, P13, and A14 (FIG. 1). Position Y19 actually has the most dramatic effect on antigenicity (only three had detectable antigenicities) with little effect on toxicity, suggesting that it may be a key antigenic determinant. In summary, these result indicate that is indeed possible to separate toxicity and antigenicity.

The most interesting residues from a vaccine perspective are those that have positive toxoidicities. This is the case for L08, C11, N12, P13, and A14, with median toxoidicities ranging from 3 (C11) to 92 (A14). Only two positions had median toxoidicities above ten, namely N12 (14) and A14 (92), and seem, on average, to be the most attractive positions to target in a vaccine. Both are receptor interacting residues.

Mutations in C07, C10, C15, and C18 had profound non-quantifiable effects on both toxicity and antigenicity, and hence do not appear in the plots or tables.

Figure 3:
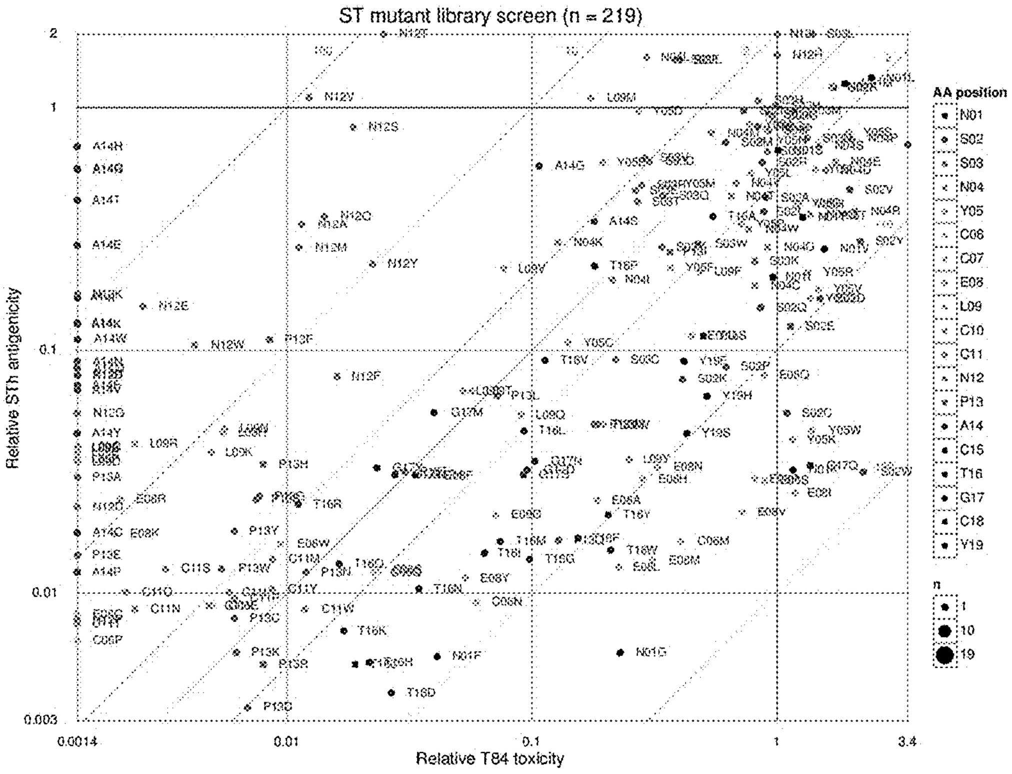
FIG. 3. T84 toxicity compared to STh antigenticity. The plot shows the relative T84 toxicity values for each STh mutant (horizontal axis) plotted against the relative STh antigenicity values (vertical axis). The axes are in logarithmic scale. The number of mutants (n) for each position that have both T84 toxicity and STh antigenicity values successfully determined 219. The points are coded with different grayscale gradient according to amino acid position from the N- to C-terminus and are labelled. The diagonal dotted lines represent toxoidicities: the black line represents a toxoidicity of 1, the grey lines to the left represents toxoidicities of 2, 10, and 100, and the grey lines to the right toxoidicities of −2, −10, and −100.

FIG. 3 show the T84 toxicity and STh antigenicity results for all individual 219 mutants that had detectable STh antigenicities.

Table 1 lists toxoid candidates that have toxoidicities of one hundred or more, and the best toxoid candidate for positions where the maximum toxoidicity is higher than ten.

STh Antigenicity Compared to STp Antigenicity

Figure 4:
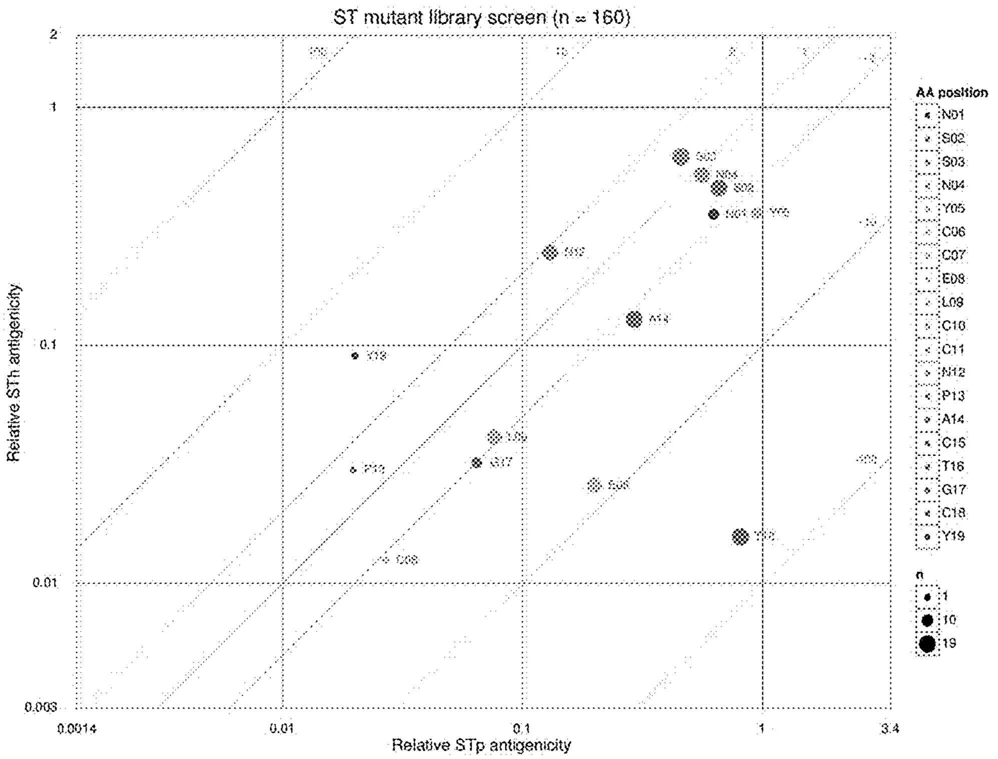
FIG. 4. STh antigenicity compared to STp antigenticity. The bubble chart shows the median relative STp antigenicity values for each amino acid position of STh (horizontal axis) plotted against the median relative STh antigenicity values (vertical axis). The axes are in logarithmic scale. The number of mutants (n) for each position that have both STh and STp antigenicity values successfully determined are visualized by the bubble sizes. A total number of 160 mutants are represented in the chart. The bubbles are coded with different grayscale gradient according to amino acid position from the N- to C-terminus and are labelled. The diagonal dotted lines represent STh antigenicity relative to STp antigenicity: the black line represents a STh antigenicity equal to STp antigenicity, the grey lines to the left represents 2-, 10-, and 100-fold increased STh antigenicities, and the grey lines to the right −2, 10-, and 100 increased STp antigenicities.

The screen was also performed with an STp ELISA. and a comparison to the STh ELISA screen results is shown in FIG. 4. In positions S03, N12, P13, and Y19, the median antigenicity was elevated 1.4 to 4.5-fold in the STh ELISA compared to the STp ELISA.

Positions N01, S02, N04, Y05, C06, E08, L09, A14, and G17 showed the opposite effect, with STp antigenicities elevated 1.1 to 7.7 fold. The most dramatic difference was observed with the T16 position, which displayed an 52-fold relative increase in STp antigenicity. This is most likely due to the fact that STh and STp differs in this position. STp has an alanine residue instead of the threonine residue of STh. In fact, the T16A mutant shows a 19-fold increase in STp antigenicity, suggesting that position 16 is a part of the epitope recognized by the anti-STp antibody. The dramatic average decrease in antigenicity in the STh ELISA suggests that T16 is also part of an STh epitope as well.

One general trend that can be observed is that the mutants seem to affect STh antigenicity more than STp antigenicity. This observation, together with the almost 10-fold higher sensitivity of the STh ELISA, suggests that the anti-STh antibody has a significantly higher affinity to STh than anti-STp antibody does (note that the anti-STh serum was protein A purified, unlike the anti-STp serum. This may also contribute to the difference in sensitivity). One likely explanation for this is the difference in position 16 of STh and STp.

Another general trend that can be observed is that mutations in the so-called toxic domain (residues 6-19) have a more dramatic effect on both STh and STp antigenicity than those of the N-terminus tail (1-5). Although one cannot rule out the possibility that the observed difference is due to differences in expression levels, it may suggest that the N-terminus is not part of an epitope recognized by the two sera.

ST Mutants Elicit Neutralizing Antibodies in Mice

Four STh mutants have been successfully purified and chemically conjugated with glutaraldehyde to bovine serum albumin (BSA): N12T, A14Q, A14T, and T16M. The A14Q is the second best toxoid candidate according to the screen (table 1) and A14T is number four. N12T is number 11 on the list of candidates (table 2), and is the third best N12 candidate. T16M is a poor toxoid candidate and was included as a control in addition to native STh.

Each of the five conjugate constructs were used to immunize five mice. All constructs elicited native STh-specific antibodies. To test for neutralizing activity, the sera resulting from the same conjugate were pooled, and used in the T84 cell assay. All five tested constructs were able to neutralize 2 ng native STh (that is proven sufficient to stimulate cGMP in T-84 cells) in the assay.

Anti-STh Antibodies Cross-React with Uroguanylin

Figure 5:
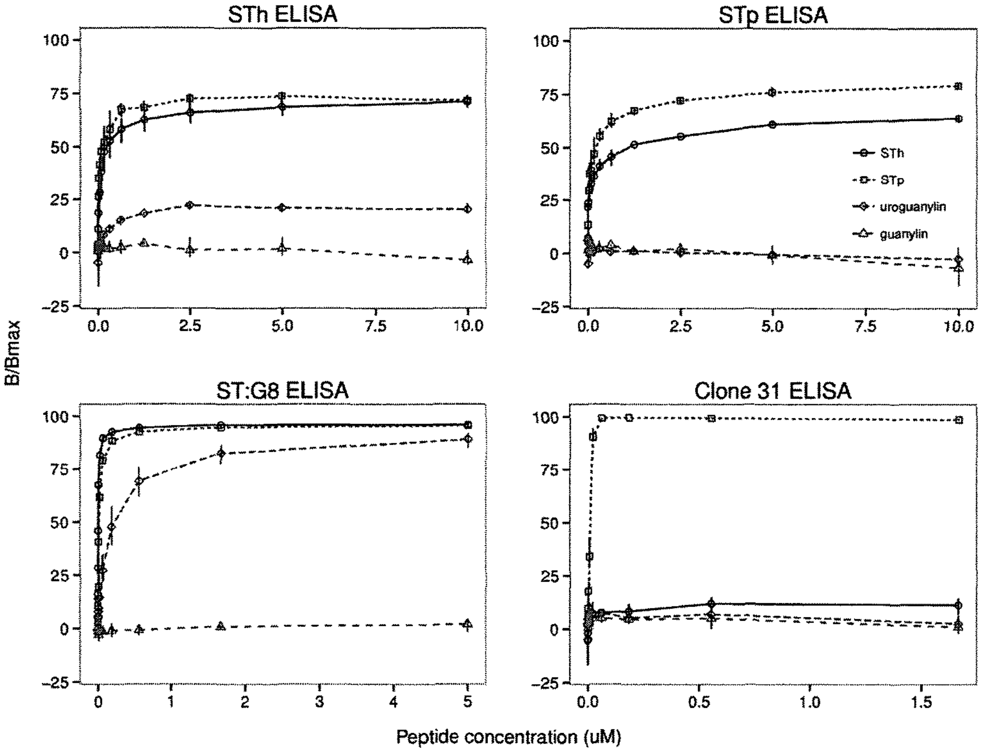
FIG. 5. The panels show results from competitive STh, STp, ST:G8, and Clone 30 ELISA experiments. Each panel displays data from three independent experiments where serial dilutions of the peptides STh, STp, uroguanylin and guanylin were tested in triplicate. Points represent the mean of all three experiments and the vertical bars outline the maximum and minimum values. The vertical axis represents a peptide's ability to outcompete binding of the antibody to the coating (B), expressed as a percentage of maximum competition (Bmax). The horizontal axis represents peptide concentration in μM.

To identify potential shared epitopes between ST and the endogenous peptides guanylin and uroguanylin, the endogenous peptides were tested against both polyclonal and monoclonal antibodies raised against STh and STp. Both polyclonal and monoclonal anti-STh antibodies bound to uroguanylin (but not guanylin) in addition to STh and STp (FIG. 5). This demonstrates that cross-reactivity is a real concern for ST vaccine development, and that it should be actively addressed in ST vaccine design. Interestingly, none of the anti-STp antibodies tested (one polyclonal and three monoclonal) displayed any cross-reactivity. This may suggest that ST vaccines should be based on STp rather than STh. However, epidemiological data suggest that STh producing ETEC is more important for disease than ETEC producing only STp and/or LT [Steinsland et al; PMID: 12447759], and is an argument for basing an ST vaccine on STh rather than STp.

Epitope Mapping of Anti-ST mAbs Suggests STh Mutation to Avoid Cross-Reactivity

Figure 6:
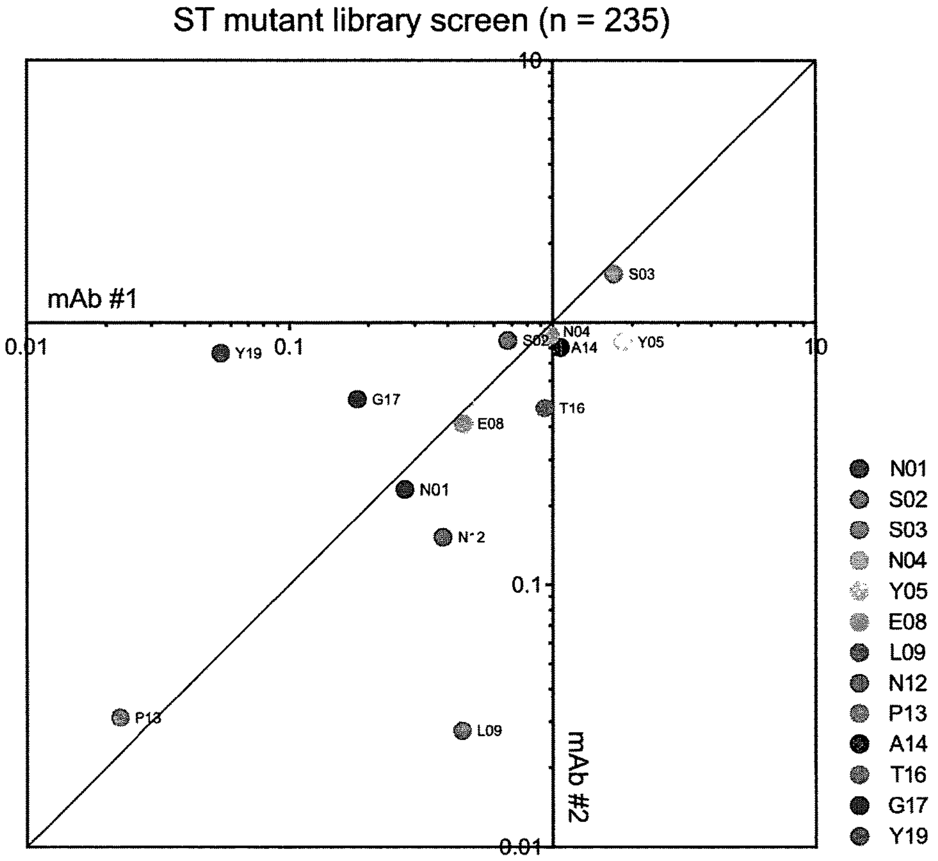
FIG. 6. ST:G8 antigenicity compared to Clone 30 antigenicity. The median relative ST:G8 antigenicity from each amino acid position of STh (vertical axis) is plotted against the median relative Clone 30 antigenicity (horizontal axis). Data from 235 individual STh mutants are represented. The bubbles are coded with different grayscale gradient according to amino acid position from the N- to C-terminus and are labelled. The diagonal line represents Clone 30 antigenicity relative to ST:G8 antigenicity.

We used the mutant library to map the epitopes of two neutralizing mAbs: the anti-STh ST:G8 mAb, and the anti-STp mAb clone 30. By analyzing the individual effects on antigenicity for all mutations in all non-cysteine residues for both mAbs, we were able to identify two distinct epitopes (FIG. 6). Mutations in L9, N12, and T16 reduce binding to ST:G8, whereas mutations in P13, G17, and Y19 reduce recognition by the anti-STp mAb. The two sets of residues form two structurally defined patches, consistent with being part of structural epitopes. Interestingly, A14 does not seem to be part of any of the epitopes as none of the 19 mutant variants of A14 displayed significantly reduced affinity to the mAbs. This is encouraging, since the A14 mutations show the most prominent decreases in toxicity.

Unlike the ST:G8 mAb, the anti-STp mAb does not cross-react with uroguanylin. This brings a new dimension to the epitope mapping. It demonstrates that it is indeed possible to generate neutralizing antibodies to ST epitopes that do not cross-react with the (uro)guanylin peptides. Common to all four STp-based antibodies is that they neutralize ST, but do not cross-react with (uro)guanylin. In the toxic domain, which is the region of similarity to the (uro)guanylin peptides, the only difference between STh and STp is the STh T16 position, which is A in STp (A15). None of the T16 mutants showed any prominent effect on Clone 30 binding, strongly suggesting that the homologous STp residue A15 is not part of the Clone 30 epitope. Hence, these data suggest that STh-based vaccines should contain a T16A mutation to circumvent cross-reactivity.

CONCLUSIONS

The screen results suggest that the two clearly most interesting positions to mutate in an attempt to make an STh toxoid are N12 and A14. These have median toxoidicities of 14 and 92, respectively.

Surprisingly, four N12 mutants apparently have antigenicities higher than native STh (N12V, N12H, N12T, and N12I). Two of these mutants have reduced toxicities relative to native STh, namely N12T (0.03) and N12V (0.01), and are toxoid candidates.

Seventeen of the nineteen mutations in position A14 lead to non-measurable toxicities (the two exceptions are A14G and A14S). The effects on relative antigenicity vary from 0.02 to 0.7. The fact that the best toxoid candidates in position A14 have antigenicities close to that of the native STh is highly encouraging.

Three other positions seem to host mutants that are moderately good toxoid candidates, namely P13, L09, and E08 (Table 1). The median toxoidicities of P13 and L09 (3 and 7.9, respectively) suggest that those positions are moderately interesting for generating STh toxoids. The median toxicity of −10.5 for E08, on the other hand, suggests that E08 is a poor position for generating STh toxoids. However, when evaluating individual E08 mutants, two interesting candidates emerge, namely E08R and E08K. Interestingly, all E08 mutants affect relative antigenicity to a similar degree, ranging from 0.008 to 0.08 (ten-fold), whereas relative toxicities vary much more, ranging from below 0.0014 to 1.2 (at least 857-fold). The results obtained with the mutants in position E08 demonstrates the strength of screening a library of all possible single amino acid mutations, rather than e.g. an alanine mutational scan.

Moreover, our data suggest that STh-based vaccines may contain a T16A mutation to circumvent cross-reactivity.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

TABLE 1

| STh mutant | Antigenicity | Toxicity | Toxoidicity |
|---|---|---|---|
| A14H | 0.6911 | 0.0014[2] | 493.64 |
| A14Q | 0.5616 | 0.0014[2] | 401.14 |
| A14R | 0.5564 | 0.0014[2] | 397.43 |
| A14T | 0.4168 | 0.0014[2] | 297.71 |
| A14E | 0.2700 | 0.0014[2] | 192.86 |
| N12K | 0.1645 | 0.5113 | 121.71 |
| A14I | 0.1645 | 0.0014[2] | 117.50 |
| L09G | 0.0403 | 0.0014[2] | 28.79 |
| P13A | 0.0301 | 0.0014[2] | 21.50 |
| E08R | 0.0244 | 0.0021 | 11.62 |
| N04L | 1.6125 | 0.2934 | 5.50 |
| C11T | 0.0075 | 0.0014[2] | 5.36 |
| C06P | 0.0064 | 0.0014[2] | 4.57 |
| S03F | 1.5714 | 0.3871 | 4.06 |
| Y05D | 0.9676 | 0.2703 | 3.58 |
| T16R | 0.0233 | 0.0111 | 2.10 |
| G17Y | 0.0329 | 0.0234 | 1.41 |
| S02N | 0.9719 | 0.7308 | 1.33 |
| N01M | 1.2547 | 1.8910 | 0.66 |
| Y19F | 0.0904 | 0.4178 | 0.22 |

TABLE 2

STh mutants ranked by toxoidicity

| Mutant | Toxoidicity |
|---|---|
| A14H | 493.64 |
| A14Q | 401.14 |
| A14R | 397.43 |
| A14T | 297.71 |
| A14E | 192.86 |
| N12K | 121.71 |
| A14I | 117.50 |
| A14L | 92.71 |
| A14K | 91.71 |
| N12V | 89.72 |
| N12T | 80.00 |
| A14W | 79.43 |
| A14N | 64.43 |
| A14M | 60.50 |
| N12E | 58.38 |
| A14D | 56.64 |
| N12R | 56.57 |
| A14F | 51.29 |
| A14V | 49.00 |
| N12S | 44.32 |
| N12G | 39.36 |
| A14Y | 32.50 |

TABLE 2-continued

STh mutants ranked by toxoidicity

| Mutant | Toxoidicity |
|---|---|
| L09G | 28.79 |
| N12A | 28.63 |
| L09S | 28.36 |
| L09A | 28.29 |
| L09E | 27.14 |
| L09P | 25.43 |
| N12W | 25.10 |
| N12Q | 25.09 |
| L09D | 24.86 |
| N12M | 23.59 |
| P13A | 21.50 |
| L09R | 17.17 |
| N12D | 16.21 |
| P13F | 13.04 |
| A14C | 12.64 |
| E08R | 11.62 |
| P13E | 10.21 |
| N12Y | 10.14 |
| E08K | 8.75 |
| A14P | 8.71 |
| L09N | 8.50 |
| L09H | 8.36 |
| L09K | 7.76 |
| L09M | 6.31 |
| E08C | 5.86 |
| N12P | 5.57 |
| N04L | 5.50 |
| A14G | 5.38 |
| C11T | 5.36 |
| N12F | 4.91 |
| C11Q | 4.59 |
| C06P | 4.57 |
| P13H | 4.25 |
| S03F | 4.06 |
| C11S | 3.94 |
| S02L | 3.92 |
| C11N | 3.58 |
| Y05D | 3.58 |
| P13G | 3.26 |
| P13S | 3.25 |
| Y05E | 3.08 |
| P13Y | 2.95 |
| L09V | 2.81 |
| P13W | 2.33 |
| N04K | 2.18 |
| N01C | 2.14 |
| C06V | 2.14 |
| C06Y | 2.14 |
| C07A | 2.14 |
| C07D | 2.14 |
| C07E | 2.14 |
| C07F | 2.14 |
| C07G | 2.14 |
| C07H | 2.14 |
| C07I | 2.14 |
| C07K | 2.14 |
| C07L | 2.14 |
| C07M | 2.14 |
| C07N | 2.14 |
| C07P | 2.14 |
| C07Q | 2.14 |
| C07R | 2.14 |
| C07S | 2.14 |
| C07T | 2.14 |
| C07V | 2.14 |
| C07W | 2.14 |
| C07Y | 2.14 |
| L09C | 2.14 |
| C10A | 2.14 |
| C10D | 2.14 |
| C10E | 2.14 |
| C10F | 2.14 |
| C10G | 2.14 |
| C10H | 2.14 |
| C10I | 2.14 |
| C10K | 2.14 |

TABLE 2-continued

STh mutants ranked by toxoidicity

| Mutant | Toxoidicity |
|---|---|
| C10L | 2.14 |
| C10M | 2.14 |
| C10N | 2.14 |
| C10P | 2.14 |
| C10Q | 2.14 |
| C10R | 2.14 |
| C10S | 2.14 |
| C10T | 2.14 |
| C10V | 2.14 |
| C10W | 2.14 |
| C10Y | 2.14 |
| C11K | 2.14 |
| C11R | 2.14 |
| N12C | 2.14 |
| N12L | 2.14 |
| C15A | 2.14 |
| C15D | 2.14 |
| C15E | 2.14 |
| C15F | 2.14 |
| C15G | 2.14 |
| C15H | 2.14 |
| C15I | 2.14 |
| C15K | 2.14 |
| C15L | 2.14 |
| C15M | 2.14 |
| C15N | 2.14 |
| C15P | 2.14 |
| C15Q | 2.14 |
| C15R | 2.14 |
| C15S | 2.14 |
| C15T | 2.14 |
| C15V | 2.14 |
| C15W | 2.14 |
| C15Y | 2.14 |
| C18A | 2.14 |
| C18D | 2.14 |
| C18E | 2.14 |
| C18F | 2.14 |
| C18G | 2.14 |
| C18H | 2.14 |
| C18I | 2.14 |
| C18K | 2.14 |
| C18L | 2.14 |
| C18M | 2.14 |
| C18N | 2.14 |
| C18P | 2.14 |
| C18Q | 2.14 |
| C18R | 2.14 |
| C18S | 2.14 |
| C18T | 2.14 |
| C18V | 2.14 |
| C18W | 2.14 |
| S03V | 2.14 |
| T16R | 2.10 |
| N12I | 2.00 |
| S03D | 1.99 |
| A14S | 1.90 |
| C11V | 1.85 |
| C06E | 1.78 |
| C11I | 1.74 |
| S03E | 1.73 |
| S03R | 1.72 |
| E08W | 1.69 |
| N12H | 1.64 |
| C11M | 1.59 |
| C11P | 1.56 |
| S03T | 1.52 |
| N04M | 1.45 |
| S03L | 1.43 |
| G17Y | 1.41 |
| G17M | 1.39 |
| Y05M | 1.35 |
| S02N | 1.33 |
| C11L | 1.30 |

TABLE 2-continued

STh mutants ranked by toxoidicity

| Mutant | Toxoidicity |
|---|---|
| P13C | 1.30 |
| L09I | 1.29 |
| S03H | 1.27 |
| S03Q | 1.27 |
| T16P | 1.24 |
| L09T | 1.20 |
| C11Y | 1.20 |
| S02M | 1.17 |
| G17W | 1.11 |
| C06R | 1.11 |
| Y05A | 1.10 |
| P13T | 1.04 |
| S02H | 1.03 |
| P13N | 1.03 |
| S03A | 1.01 |
| S02G | 1.00 |
| S03G | 0.97 |
| N04I | 0.92 |
| G17H | 0.92 |
| P13K | 0.92 |
| N04F | 0.91 |
| P13L | 0.90 |
| S03P | 0.87 |
| Y05N | 0.85 |
| S03M | 0.83 |
| T16Q | 0.81 |
| T16V | 0.81 |
| E08F | 0.79 |
| S03Y | 0.78 |
| Y05C | 0.77 |
| N04A | 0.73 |
| C11W | 0.73 |
| S03I | 0.72 |
| N04V | 0.72 |
| S02F | 0.71 |
| P13I | 0.69 |
| Y05L | 0.69 |
| S02R | 0.68 |
| N04T | 0.67 |
| N01M | 0.66 |
| N01S | 0.66 |
| T16A | 0.65 |
| P13R | 0.64 |
| L09Q | 0.60 |
| Y05F | 0.59 |
| C06W | 0.59 |
| S03W | 0.57 |
| S03N | 0.56 |
| N01L | 0.55 |
| C06S | 0.54 |
| C06Q | 0.54 |
| T16L | 0.50 |
| P13D | 0.49 |
| S02A | 0.47 |
| N04S | 0.47 |
| Y05P | 0.47 |
| C06D | 0.46 |
| L09F | 0.43 |
| S02I | 0.42 |
| S03C | 0.42 |
| T16K | 0.41 |
| N04W | 0.41 |
| Y05S | 0.41 |
| Y05I | 0.39 |
| C06T | 0.37 |
| N04P | 0.37 |
| N04D | 0.35 |
| N04E | 0.35 |
| G17N | 0.34 |
| Y05G | 0.34 |
| G17D | 0.34 |
| G17S | 0.33 |
| Y05H | 0.33 |
| T16N | 0.30 |
| E08G | 0.30 |
| N04G | 0.29 |

TABLE 2-continued

STh mutants ranked by toxoidicity

| Mutant | Toxoidicity |
|---|---|
| S03K | 0.29 |
| N01T | 0.28 |
| P13V | 0.28 |
| P13M | 0.27 |
| T16C | 0.27 |
| N04Q | 0.27 |
| E08D | 0.26 |
| L09W | 0.25 |
| T16H | 0.24 |
| S02V | 0.23 |
| Y05T | 0.23 |
| T16S | 0.23 |
| T16I | 0.23 |
| N04C | 0.23 |
| T16M | 0.22 |
| Y19F | 0.22 |
| E08Y | 0.21 |
| N01I | 0.21 |
| S02T | 0.21 |
| S02K | 0.18 |
| N04R | 0.18 |
| S02Q | 0.18 |
| N01V | 0.17 |
| Y05R | 0.16 |
| C06N | 0.16 |
| T16D | 0.15 |
| L09Y | 0.14 |
| Y19C | 0.14 |
| C06K | 0.14 |
| T16G | 0.14 |
| S02P | 0.14 |
| N01F | 0.13 |
| E08A | 0.13 |
| P13Q | 0.13 |
| S02Y | 0.13 |
| Y19H | 0.12 |
| Y05V | 0.12 |
| Y05Q | 0.12 |
| S02E | 0.11 |
| S02D | 0.11 |
| T16F | 0.11 |
| Y19S | 0.11 |
| E08H | 0.10 |
| G17V | 0.10 |
| G17F | 0.10 |
| T16Y | 0.10 |
| E08N | 0.10 |
| N01E | 0.09 |
| G17K | 0.09 |
| G17R | 0.09 |
| E08Q | 0.09 |
| G17I | 0.09 |
| C06H | 0.08 |
| G17C | 0.08 |
| G17P | 0.08 |
| C06A | 0.08 |
| T16W | 0.07 |
| C06I | 0.07 |
| G17T | 0.07 |
| G17L | 0.07 |
| E08L | 0.06 |
| S02C | 0.05 |
| Y19D | 0.05 |
| G17E | 0.05 |
| E08M | 0.04 |
| C06L | 0.04 |
| N01W | 0.04 |
| C06M | 0.04 |
| T16E | 0.04 |
| C06F | 0.04 |
| Y19K | 0.04 |
| Y19P | 0.04 |
| Y05K | 0.04 |
| Y19E | 0.04 |
| E08P | 0.04 |
| Y05W | 0.03 |
| E085 | 0.03 |
| E08V | 0.03 |
| N01Y | 0.03 |
| N01K | 0.03 |
| N01D | 0.03 |
| Y19T | 0.03 |
| N01G | 0.02 |
| G17Q | 0.02 |
| N01H | 0.02 |
| E08I | 0.02 |
| Y19R | 0.02 |
| C06G | 0.02 |
| G17A | 0.02 |
| N01A | 0.01 |
| N04Y | 0.01 |
| S02W | 0.01 |
| C18Y | 0.01 |
| N01P | 0.01 |
| Y19G | 0.01 |
| Y19I | 0.01 |
| Y19N | 0.01 |
| N01Q | 0.01 |
| Y19V | 0.01 |
| E08T | 0.01 |
| Y19Q | 0.01 |
| Y19L | 0.01 |
| Y19M | 0.01 |
| Y19W | 0.01 |
| Y19A | 0.00 |
| N01R | 0.00 |
| N04H | 0.00 |

The invention claimed is:

1. A mutant of an *E. coli* heat-stable toxin (ST) having the following wild-type sequence:

NSSNYCCELCCNPACTGCY (SEQ ID NO: 1)

wherein the mutant has one or two mutations, and wherein the mutant comprises a mutation selected from the group consisting of: A14T and N12T.

2. The mutant according to claim 1 wherein the mutant comprises an A14T mutation.

3. The mutant according to claim 1 wherein the mutant has a first mutation that is A14T and a second mutation selected from N12K, N12V, N12T, N12E, N12R, N12S, N12G, N12A, N12W, N12Q, L9G, L9S, L9A, L9E, L9P, L9D, L9R, P13A, P13F, P13E, C11H, E8R, and E8K.

4. The mutant according to claim 1 wherein the mutant has a first mutation that is N12T and a second mutation selected from A14T, A14H, A14Q, A14R, A14E, A14I, A14L, A14K, A14W, A14N, A14M, A14D, A14F, A14V, A14Y, A14C, L9G, L9S, L9A, L9E, L9P, L9D, L9R, P13A, P13F, P13E, C11H, E8R, and E8K.

5. The mutant according to claim 1 further comprising a T16A mutation.

6. The mutant according to claim 3 wherein the mutant has the following mutations: A14T and N12K.

7. The mutant according to claim 1 wherein the mutant has a single A14T point mutation.

8. A mutant of an *E. coli* heat-stable toxin (ST) having the following wild-type sequence:

NSSNYCCELCCNPACTGCY (SEQ ID NO:1)

wherein the mutant has two mutations, and wherein the mutant has a mutation at position T16 in combination with a mutation at position N12 or A14.

9. The mutant according to claim 8 having a T16A mutation in combination with a mutation selected from A14T, A14H, A14Q, A14R, A14E, A14I, A14L, A14K, A14W, A14N, A14M, A14D, A14F, A14V, and A14Y.

10. The mutant according to claim 8 having a T16A mutation in combination with a mutation selected from N12K, N12V, N12T, N12E, N12R, N12S, N12G, N12A, N12W and N12Q.

11. The mutant according to claim 8 wherein the mutant has the following mutations: A14T and T16A.

12. The mutant according to claim 8 wherein the mutant has the following mutations: N12K and T16A.

13. A mutant of an *E. coli* heat-stable toxin (ST) having the following wild-type sequence:

NTFYCCELCCNPACAGCY (SEQ ID NO: 2)

wherein the mutant has one or two mutations, and wherein the mutant comprises a mutation selected from the group consisting of: A13T and N11T.

14. The mutant according to claim 13 wherein the mutant comprises an A13T mutation.

15. The mutant according to claim 13 wherein the mutant has a first mutation that is A13T and a second mutation selected from N11K, N11V, N11T, N11E, N11R, N11S, N11G, N11A, N11W, N11Q, L8G, L8S, L8A, L8E, L8P, L8D, L8R, P12A, P12F, P12E, C10H, E7R, and E7K.

16. The mutant according to claim 13 wherein the mutant has a first mutation that is N11T and a second mutation selected from A13T, A13H, A13Q, A13R, A13E, A13I, A13L, A13K, A13W, A13N, A13M, A13D, A13F, A13V and A13Y.

17. The mutant according to claim 15 wherein the mutant has the following mutations: A13T and N11K.

18. The mutant according to claim 13 wherein the mutant has a single A13T point mutation.

19. A mutant according to claim 1, 8, or 13, wherein the mutant is coupled to a carrier.

20. A vaccine composition comprising the mutant according to claim 1, 8, or 13, and a pharmaceutically acceptable carrier or excipient.

* * * * *

SEQUENCE LISTING

<160> NUMBER OF SEQ ID NOS: 8

<210> SEQ ID NO 1
<211> LENGTH: 19
<212> TYPE: PRT
<213> ORGANISM: Escherichia coli

<400> SEQUENCE: 1

Asn Ser Ser Asn Tyr Cys Cys Glu Leu Cys Cys Asn Pro Ala Cys Thr
1 5 10 15

Gly Cys Tyr

<210> SEQ ID NO 2
<211> LENGTH: 18
<212> TYPE: PRT
<213> ORGANISM: Escherichia coli

<400> SEQUENCE: 2

Asn Thr Phe Tyr Cys Cys Glu Leu Cys Cys Asn Pro Ala Cys Ala Gly
1 5 10 15

Cys Tyr

<210> SEQ ID NO 3
<211> LENGTH: 19
<212> TYPE: PRT
<213> ORGANISM: Artificial Sequence
<220> FEATURE:
<223> OTHER INFORMATION: Mutant sequence

<400> SEQUENCE: 3

Asn Ser Ser Asn Tyr Cys Cys Glu Leu Cys Cys Asn Pro His Cys Thr
1 5 10 15

Gly Cys Tyr

<210> SEQ ID NO 4
<211> LENGTH: 19
<212> TYPE: PRT
<213> ORGANISM: Artificial Sequence
<220> FEATURE:
<223> OTHER INFORMATION: Mutant sequence

<400> SEQUENCE: 4

Asn Ser Ser Asn Tyr Cys Cys Glu Leu Cys Cys Asn Pro Thr Cys Thr
1 5 10 15

Gly Cys Tyr

<210> SEQ ID NO 5
<211> LENGTH: 19
<212> TYPE: PRT
<213> ORGANISM: Artificial Sequence
<220> FEATURE:
<223> OTHER INFORMATION: Mutant sequence

<400> SEQUENCE: 5

Asn Ser Ser Asn Tyr Cys Cys Glu Leu Cys Cys Thr Pro Ala Cys Thr
1 5 10 15

Gly Cys Tyr

<210> SEQ ID NO 6
<211> LENGTH: 18
<212> TYPE: PRT
<213> ORGANISM: Artificial Sequence
<220> FEATURE:
<223> OTHER INFORMATION: Mutant sequence

<400> SEQUENCE: 6

Asn Thr Phe Tyr Cys Cys Glu Leu Cys Cys Asn Pro His Cys Ala Gly
1 5 10 15

Cys Tyr

<210> SEQ ID NO 7
<211> LENGTH: 18
<212> TYPE: PRT
<213> ORGANISM: Artificial Sequence
<220> FEATURE:
<223> OTHER INFORMATION: Mutant sequence -continued

```
<400> SEQUENCE: 7

Asn Thr Phe Tyr Cys Cys Glu Leu Cys Cys Asn Pro Thr Cys Ala Gly
1               5                   10                  15

Cys Tyr


<210> SEQ ID NO 8
<211> LENGTH: 18
<212> TYPE: PRT
<213> ORGANISM: Artificial Sequence
<220> FEATURE:
<223> OTHER INFORMATION: Mutant sequence

<400> SEQUENCE: 8

Asn Thr Phe Tyr Cys Cys Glu Leu Cys Cys Thr Pro Ala Cys Ala Gly
1               5                   10                  15

Cys Tyr
```